United States Patent
Tourel et al.

(10) Patent No.: US 12,214,011 B2
(45) Date of Patent: Feb. 4, 2025

(54) SELECTIVE CELL DEATH-INDUCING ENZYME SYSTEM

(71) Applicant: Sylvain Tourel, Hattingen (DE)

(72) Inventors: Sylvain Tourel, Hattingen (DE); Tabea Kräft, Dortmund (DE)

(73) Assignee: Sylvain Tourel, Hattingen (DE)

( * ) Notice: Subject to any disclaimer, the term of this patent is extended or adjusted under 35 U.S.C. 154(b) by 1246 days.

(21) Appl. No.: 16/493,605

(22) PCT Filed: Mar. 13, 2018

(86) PCT No.: PCT/EP2018/056313
§ 371 (c)(1),
(2) Date: Sep. 12, 2019

(87) PCT Pub. No.: WO2018/167105
PCT Pub. Date: Sep. 20, 2018

(65) Prior Publication Data
US 2022/0370555 A1   Nov. 24, 2022

(30) Foreign Application Priority Data

Mar. 13, 2017   (EP) ..................................... 17160694

(51) Int. Cl.
*A61K 38/17* (2006.01)
*A61K 38/48* (2006.01)
*A61K 48/00* (2006.01)
*A61P 35/00* (2006.01)

(52) U.S. Cl.
CPC ...... *A61K 38/1761* (2013.01); *A61K 38/4873* (2013.01); *A61K 48/005* (2013.01); *A61P 35/00* (2018.01)

(58) Field of Classification Search
CPC ............ A61K 38/1761; A61K 38/4873; A61K 48/005; A61P 35/00; C07K 14/005; C07K 2319/50; C12N 2770/34022; C12N 2770/34033; C12N 2800/107; C12N 9/6472; C12N 9/503; C12Y 304/22044
See application file for complete search history.

(56) References Cited

U.S. PATENT DOCUMENTS

| | | | |
|---|---|---|---|
| 2003/0054000 A1 | 3/2003 | Dowdy | |
| 2003/0086919 A1 | 5/2003 | Rosenblum et al. | |
| 2008/0312130 A1 | 12/2008 | Kaneda et al. | |
| 2009/0081157 A1 | 3/2009 | Kornbluth et al. | |
| 2016/0038573 A1* | 2/2016 | Tourel ................ | A61K 38/4873 424/94.2 |

FOREIGN PATENT DOCUMENTS

| | | |
|---|---|---|
| EP | 01873251 A1 | 1/2008 |
| JP | 2002-505077 A | 2/2002 |
| JP | 2004-535202 A | 11/2004 |
| JP | 2005-278630 A | 10/2005 |
| JP | 2008-521398 A | 10/2007 |
| JP | 2006-518737 A | 8/2008 |
| JP | 2008-308440 A | 12/2008 |
| JP | 2009-522372 A | 6/2009 |
| JP | 2010-500967 A | 1/2010 |
| JP | 2016-510324 A | 4/2016 |
| WO | 2006/057500 A1 | 6/2006 |
| WO | 2008011157 A2 | 1/2008 |
| WO | 2014111553 A1 | 7/2014 |
| WO | 2016/186575 A1 | 11/2016 |

OTHER PUBLICATIONS

Gray DC et al. Activation of Specific Apoptotic Caspases with an Engineered Small-Molecule-Activated Protease (Cell 2010 142(4) 637-646) (Year: 2010).*
Pan Q et al. SMAC-armed vaccinia virus induces both apoptosis and necroptosis and synergizes the efficiency of vinblastine in HCC. Human Cell 2014, 27 162-171 (Year: 2014).*
Li J et al. Caspases in apoptosis and beyond. Oncogene 2008 27 6194-6206 (Year: 2008).*
Cesaratto F et al. Tobacco Etch Virus protease: A shortcut across biotechnologies. J of Biotech 2016 231 pp. 239-249 (Year: 2016).*
Straszewski-Chavez SL et al. XAF1 Mediates Tumor Necrosis Factor-α-induced Apoptosis and X-linked Inhibitor of Apoptosis Cleavage by Acting through the Mitochondrial Pathway. JBC 2007 282(17) p. 13059-13072 (Year: 2007).*
International Search Report and Written Opinion dated May 18, 2018, International Application No. PCT/EP2018/056313.
Putt K S et al., "Small-molecule activation of procaspase-3 to casepase-3 as a personalized anticancer strategy", Nature Chemical Biology, vol. 2, No. 10, Oct. 2006, pp. 543-550.
Search Report from Japanese Application No. 2019-571779 dated Nov. 8, 2021.
Notice of Reasons for Refusal from Japanese Application No. 2019-571779 dated Dec. 10, 2021.
Goping et al. "Granzyme B-induced apoptosis requires both direct caspase activation and relief of caspase inhibition," Mar. 2003;18(3):355-65.
Lee et al. "XAF1 directs apoptotic switch of p53 signaling through activation of HIPK2 and ZNF313," PNAS Oct. 28, 2014; 111 (43) pp. 15532-15537.
Morgan, et al., "Protein and Cellular Engineering Platform for Selective Inducible Apoptotic Proteolysis," Protein Science vol. 24, Issue S Jan. 2015.

* cited by examiner

*Primary Examiner* — Karen A. Canella
*Assistant Examiner* — John J Skoko, III
(74) *Attorney, Agent, or Firm* — Troutman Pepper Hamilton Sanders LLP; Chris N. Davis

(57) ABSTRACT

The invention relates to a fusion protein containing a selective cell death-inducing enzyme system for use in the therapy and/or treatment of cancer and tumors in humans and animals, a process, and its use.

14 Claims, 3 Drawing Sheets

Specification includes a Sequence Listing.

TEV protease cleavage sites are indicated as [[blank]] black boxes. The figure refers to SEQ ID [[no.]] NO: 13.

SELECTIVE CELL DEATH-INDUCING ENZYME SYSTEM

CROSS-REFERENCE TO RELATED APPLICATIONS

This application is a U.S. National Phase of International Patent Application No. PCT/EP2018/056313, filed Mar. 13, 2018, which claims priority to European Patent Application No. 17160694.0, filed Mar. 13, 2017, both of which applications are herein incorporated by reference in their entireties.

SEQUENCE LISTING

This application contains a Sequence Listing which has been submitted in ASCII format via EFS-Web and is hereby incorporated by reference herein in its entirety. The ASCII text file was created on Feb. 21, 2020, is named 255829.000001_ST25.txt and is 40,246 bytes in size.

DESCRIPTION

The invention relates to a fusion protein containing a selective cell death-inducing enzyme system for use in the therapy and/or treatment of cancer and tumors in humans and animals, a process, and its use.

Cancer is a class of diseases that are characterized by uncontrolled cell growth and the dissemination of degenerate cells in the body and, in the case of metastasis, ultimately lead to the death of the patient. The treatment of tumors and cancer diseases depends strongly on the type of the tumor that appears and today usually involves the use of radiation therapy or chemotherapy, in addition to invasive surgery. Cancer diseases are triggered both by external factors (tobacco smoking, infectious organisms or viruses, mutagens, and ionizing radiation) and also by internal factors (genetic predisposition, hormones, immune system factors and spontaneous somatic mutations). Cancer can also be treated by immunotherapy, hormone therapy, and also by targeted therapy. The advantages of using chemotherapy to kill tumor cells are justified by its ability to interrupt cell division by exerting a destructive effect on the cellular DNA or RNA. As soon as the tumor cells can no longer divide, they die. The more quickly the cells divide, the higher the probability that they can be killed by the chemotherapeutic agent and that a tumor will shrink by the induction of cell death. Consequently, chemotherapy acts most efficiently on cells that divide quickly. However, chemotherapy is unable to distinguish between cancer/tumor cells and rapidly growing normal cells of the body, so that side effects such as hair loss, fatigue, pain, blood count changes, and nausea occur. Chemotherapy is divided into five large classes based on the mechanism of action: alkylating agents, plant alkaloids, antitumor antibiotics, and antimetabolites.

So-called targeted therapies exploit our knowledge of the differences of cancer cells from normal healthy cells. Targeted therapy is intended to eliminate cancer cells by exploiting specific features of these cancer cells so that there is no damage to normal, healthy cells. The active ingredients of such targeted therapies comprise especially monoclonal antibodies that specifically recognize and bind to the cancer cells, and angiogenesis inhibitors that specifically inhibit the growth of the blood vessels that supply the tumor. For the most part, targeted therapy uses small organic molecules that can penetrate the cancer cell membrane and block cellular metabolism, and especially to trigger apoptosis, killing the cells. A number of active ingredients have been described that target intracellular signal pathways to trigger such apoptosis. Other active ingredients recognize and bind to tumor-specific receptors on the cell surface.

However, these therapies place an extraordinary burden on the immune system, and in many cases, can only be used to a limited extent. In addition, for the most part these forms of therapy require long pauses between the individual treatments for regeneration of the immune system. Therefore, in recent years especially gene therapy approaches or genetic vaccination have turned out to be promising for treatment, or in support of these classic measures.

Gene therapy and genetic vaccination are molecular medical procedures whose general use in the therapy and prevention of diseases have considerable impact on medical practice. Both procedures are based on the introduction of nucleic acids or peptides into the patient's cells or tissue, and on these cells or tissue then processing the information encoded by the introduced nucleic acids, i.e., on the expression of the desired polypeptides.

The usual approach of existing gene therapy and genetic vaccination procedures is to use DNA to introduce the required genetic information into the cell. In this connection, various procedures have been described to introduce DNA into cells, such as calcium phosphate transfection, Polybrene® transfection, protoplast fusion, electroporation, microinjection, and lipofection.

Another procedure that has been proposed, especially for genetic vaccination, is the use of DNA viruses as a DNA vehicle. Such viruses have the advantage that their infectious properties allow them to achieve a very high transfection rate.

Elimination of disease related cells by the physiological process of apoptosis is highly beneficial for patients. In contrast to other forms of cell death, apoptosis is a highly regulated and controlled process that confers several advantages. Apoptotic cells die very fast and produced cell fragments called apoptotic bodies are removed by phagocytic cells. Thereby surrounding cells are protected from any damage (Kreitman R J: Immunotoxins in cancer therapy. Current Opinion in Immunology 1999, 11:570-578).

Moreover, other death inducers such as immunotoxins of plant or bacterial origin often face the problem of the development of neutralizing antibodies. The immunogenicity of those agents is considered a major barrier to the clinical utility.

However, cancer cells are known to resist apoptotic insults, which enables tumor initiation and progression. The defective or inefficient apoptosis signaling is often caused by mutations leading to the upregulation of pro-survival proteins or suppression of proapoptotic proteins.

Apoptosis of a cell can be induced by various proapoptotic mechanisms and proteins. What these mechanisms and proteins have in common is that they activate a cascade of proteolytic cysteine proteases, called caspases, directed against cells. This cascade involves the initially activated caspases, such as, for example, caspase 8 and caspase 9, activating the effector cascade, such as, for example, caspases 3 and 6 or 7. These in turn cleave a series of cellular substrates, causing the apoptosis of the affected cell.

In the context of this invention, the term "programmed cell death" can be used as a synonym for "apoptosis". As defined in this invention, an "induced cell death" is one in which an active substance triggers apoptosis or programmed cell death, preferably by means of a caspase.

However, it is known that caspases can be used for tumor treatment, e.g. as disclosed in US20030054000A1.

Induction of apoptosis by delivering caspases 3, 7, 8 or 10 can evade all dysfunctions of the apoptosis pathway upstream of these enzymes. Caspases, in particular caspase 3, caspase 7, caspase 8 or caspase 10 have a dominant role in the apoptosis pathway, they provide over one hundred protein targets in the cell. In contrast to other caspases, caspase 3, caspase 7, caspase 8 or caspase 10 alone or together are able to induce apoptosis when delivered to cancer cells.

However, also several caspases 3, 7, 8 or 10 resistant cancer cells exist. These cells express elevated levels of inhibitors of apoptosis proteins (IAPs) which are naturally occurring intra-cellular proteins that suppress caspase-dependent apoptosis.

There are a series of proteases that are only enzymatically active on substrate proteins that have a specific recognition sequence. The following table lists some examples. P1 designates the position of the amino acid after which the cleavage takes place, P4, P3, and P2 are the N-terminal positions before the restriction site P1. P1' and P2' are the C-terminal positions following P1. This means that the proteases cleave the polypeptide chain between P1 and P1'.

Usually, caspase(s) 3, 7, 8, 10 are translated as inactive zymogen that is natural cleaved e.g. by granzyme B. The procaspase(s) 3, 7, 8, 10 genes, consist of an N-terminal prodomain which is followed by two components, the so called small and the large subunit (Earnshaw W C, Martins L M, Kaufmann S H: Mammalian caspases: structure, activation, substrates, and functions during apoptosis. Annu Rev Biochem 1999, 68:383-424). The sites of processing are located at the junction of the prodomain and large subunit and at the intersubunit linker between the two subunits. All natural cleavages necessary for caspase maturation occur on the carboxyl side of an aspartate residue (termed the P1' residues, cf. Table 1).

It has been reported, that cleavage of the intersubunit linker is required and sufficient to induce activity. Therefore, the preferred caspases 3, 7, 8, 10 variants used according to the invention are equipped with a TEV protease cleavage site at the P1' position between the small and large subunit of the said caspases preferably presenting serine (S). Thereby, the endogenous P1' Aspartate (D)), which is critical for the cleavage by granzyme B is removed and the by TEV protease preferred serine (S) as P1' is naturally provided.

TABLE 1

| Protease | Restriction site | | | | | |
|---|---|---|---|---|---|---|
| | P4 | P3 | P2 | P1 | P1' | P2' |
| Caspase 1 | F, W, Y or L | — | H, A or T | D | not P, E, D, Q, K or R | — |
| Caspase 2 | D | V | A | D | not P, E, D, Q, K or R | — |
| Caspase 3 | D | M | Q | D | not P, E, D, Q, K or R | — |
| Caspase 4 | L | E | V | D | not P, E, D, Q, K or R | — |
| Caspase 5 | L or W | E | H | D | — | — |
| Caspase 6 | V | E | H or I | D | not P, E, D, Q, K or R | — |
| Caspase 7 | D | E | V | D | not P, E, D, Q, K or R | — |
| Caspase 8 | I or L | E | T | D | not P, E, D, Q, K or R | — |
| Caspase 9 | L | E | H | D | — | — |
| Caspase 10 | I | E | A | D | — | — |
| Clostripain (Clostridiopeptidase B) | — | — | — | R | — | — |
| Enterokinase | D or N | D or N | D or N | K | — | — |
| Factor Xa | A, F, G, I, L, T, V or M | D or E | G | R | — | — |
| Granzyme B | I | E | P | D | — | — |
| *Staphylococcus* Peptidase I (V8 Protease) | — | — | not E | E | — | — |
| Thrombin | — | — | G | R | G | — |
| | A, F, G, I, L, T, V or M | A, F, G, I, L, T, V, W or A | P | R | not D, E | not D, E |

Amino Acids Designated Using One-Letter Code

Especially effective and specific caspases (see Table 1) are caspases 3, 7, 8 and 10.

Starting from this prior art, the inventor's goal was to bring about the induced cell death of a cancer or tumor cell by means of an active ingredient.

Caspases are expressed as inactive zymogens and require a specific cleavage for activation. For the purpose of specifically activating caspase(s) 3, 7, 8, 10 in accordance with the present invention their natural cleavage site is replaced by an amino acid sequence (recognition site) that is uniquely cleaved by tobacco etch virus protease (abbreviated hereinafter as "TEV").

Furthermore, placing the recognition site between two domains ensured advantageously surface accessibility.

Surprisingly, it is possible for tumor cells to die by means of a cell death-inducing enzyme system comprising a fusion protein containing an inactive form of caspase 3 and/or caspase 7 and/or caspase 8 and/or caspase 10, or a nucleic acid encoding it, and TEV (SEQ ID no. 1 or SEQ ID no. 2), or a nucleic acid encoding it, wherein caspase(s) 3, 7, 8, 10 is/are provided in altered form comprising at least one recognition site (recognition sequences) ENLYFQS (SEQ ID no. 3) and/or ENLYFQG (SEQ ID no. 4) for TEV.

According to the invention, TEV recognizes the recognition site (recognition sequence) ENLYFQS (SEQ ID no. 3) or ENLYFQG (SEQ ID no. 4) in an altered form of caspase 3 and/or caspase 7 and/or caspase 8 and/or caspase 10, wherein the recognition site (recognition sequence) is preferably linked (ligated) between the large and small subunits of caspase 3 and/or caspase 7 and/or caspase 8 and/or caspase 10.

Such a sequence can be defined as follows:

```
Altered caspase 3 with recognition site for TEV
in bold (SEQ ID no. 5):
MENTENSVDS KSIKNLEPKI IHGSESMDSG ISLDNSYKMD

YPEMGLCIII MTSRSGTDVD AANLRETFRN LKYEVRNKND

LTREEIVELM RDVSKEDHSK RSSFVCVLLS HGEEGIIFGT

NGPVDLKKIT NFFRGDRCRS LTGKPKLFII QACRCTELDC

GIETENLYFQ SGVDDDMACH KIPVEADFLY AYSTAPGYYS

WRNSKDGSWF IQSLCAMLKQ YADKLEFMHI LTRVNRKVAT

EFESFSFDAT FHAKKQIPCI VSMLTKELYF YH

Altered caspase 7 with recognition site for TEV
in bold (SEQ ID no. 6):
ADDQGCIEEQGVEDSANEDSVDAKPDRSSFVPSLFSKKKKNVTMRSIKTT

RDRVPTYQYNMNFEKLGKCIIINNKNFDKVTGMGVRNGTDKDAEALFKCF

RSLGFDVIVYNDCSCAKMQDLLKKASEEDHTNAACFACILLSHGEENVIY

GKDGVTPIKDLTAHFRGDRCKTLLEKPKLFFIQACRGTELDDGIQAENLY

FQSGPINDTDANPRYKIPVEADFLFAYSTVPGYYSWRSPGRGSWFVQALC

SILEEHGKDLEIMQILTRVNDRVARHFESQSDDPHFHEKKQIPCVVSMLT

KELYGFSQ

Altered caspase 8 with recognition site for TEV
in bold (SEQ ID no. 7):
MDSESQTLDKVYQMKSKPRGYCLIINNHNFAKAREKVPKLHSIRDRNGTH

LDAGALTTTFEELHFEIKPHDDCTVEQIYEILKIYQLMDHSNMDCFICCI

LSHGDKGIIYGTDGQEAPIYELTSQFTGLKCPSLAGKPKVFFIQACQGDN

YQKGIPVETDSENLYFQGMDLSSPQTRYIPDEADFLLGMATVNNCVSYRN

PAEGTWYIQSLCQSLRERCPRGDDILTILTEVNYEVSNKDDKKNMGKQMP

QPTFTLRKKLVFPSD

Altered caspase 10 with recognition site for TEV
in bold (SEQ ID no. 8):
MDVKTFLEALPQESWQNKHAGSNGNRATNGAPSLVSRGMQGASANTLNSE

TSTKRAAVYRMNRNHRGLCVIVNNHSFTSLKDRQGTHKDAEILSHVFQWL

GFTVHIHNNVTKVEMEMVLQKQKCNPAHADGDCFVFCILTHGRFGAVYSS

DEALIPIREIMSHFTALQCPRLAEKPKLFFIQACQGEEIQPSVSIEAENL

YFQGQAPTSLQDSIPAEADFLLGLATVPGYVSFRHVEEGSWYIQSLCNHL

KKLVPRMLKFLEKTMEIRGRKRTVWGAKQISATSLPTAISAQTPRPPMRR

WSSVS
```

Therefore, the goal is achieved in its full scope by the claims that have been drawn up.

As soon as the inactive form of caspase 3 and/or caspase 7 and/or caspase 8 and/or caspase 10 and TEV are introduced together into a tumor cell and expressed (if applicable), TEV releases the active form of caspase 3 and/or caspase 7 and/or caspase 8 and/or caspase 10, inducing cell death through apoptosis or programmed cell death.

The inventive selection of caspase 3 and/or caspase 7 and/or caspase 8 and/or caspase 10 used in the invention and the means used, namely TEV, to unmask an inactive form of caspase 3 and/or caspase 7 and/or caspase 8 and/or caspase 10 into an active form, are especially advantageous. As soon as these two polypeptides are present in a tumor cell, the unmasking proceeds in a completely specific and efficient manner. Here it is especially advantageous that neither procaspases nor TEV occur in humans or mammals.

TEV is referred to in the document Kapust et al, The P1' specificity of tobacco etch virus protease, Biochemical and Biophysical Research Communications, 294 (2002) 949-955. TEV refers to the catalytically active 27 kDa C-terminal domain of the nuclear inclusion a (NIa) protease from tobacco etch virus (Dougherty W G, Parks T D, Cary S M, Bazan J F, Fletterick R J: Characterization of the catalytic residues of the tobacco etch virus 49-kDa proteinase. Virology 1989, 172:302-310). The protease recognizes the seven-residue target sequence ENLYFQ/S, where "/" denotes the cleaved peptide bond. The serine P1' residue can be substituted by several other amino acids with relatively little impact on the efficiency of processing. Its highly stringent sequence specificity makes TEV protease a useful reagent for controlled intracellular processing of fusion proteins in vitro and in vivo. The recognized sequence does not occur in the human proteome which makes its application relatively nontoxic in vivo (Kapust R B, Waugh D S: Controlled intracellular processing of fusion proteins by TEV protease. Protein Expr Purif 2000, 19 (2):312-318).

Therefore, the invention relates to a drug or fusion protein comprising an inactive form of caspase 3 and/or caspase 7 and/or caspase 8 and/or caspase 10, or a nucleic acid encoding it, and TEV (e.g., SEQ ID no. 1 or SEQ ID no. 2), or a nucleic acid encoding it. TEV recognizes the recognition sites (recognition sequences) ENLYFQS (SEQ ID no. 3) or ENLYFQG (SEQ ID no. 4) in the inactive form of altered caspase 3 and/or altered caspase 7 and/or altered caspase 8 and/or altered caspase 10, like SEQ ID no. 5 or SEQ ID no. 6 or SEQ ID no. 7 or SEQ ID no. 8.

In a preferred embodiment of the invention, the inactive form of caspase 3 and/or caspase 7 and/or caspase 8 and/or caspase 10 is an altered "procaspase" (SEQ ID no. 5 or SEQ ID No.6 or SEQ ID no. 7 or SEQ ID no. 8) or a nucleic acid encoding it.

In another preferred embodiment of the invention, the inactive form of caspase 3 and/or caspase 7 and/or caspase 8 and/or caspase 10 is a fusion protein or a nucleic acid encoding it, wherein at least one sequence selected from the group of SEQ ID no. 9, 10, 11, 12, 13, 14, 15, 16 is obtained or released through cleavage by TEV (e.g., SEQ ID no. 1 or SEQ ID no. 2) at ENLYFQ (SEQ ID no. 3) or ENLYFQG (SEQ ID no. 4).

Therefore, the invention relates to an inactive form of caspase 3 and/or caspase 7 and/or caspase 8 and/or caspase 10, namely a fusion protein comprising SEQ ID no. 5, 6, 7 or 8 or a nucleic acid encoding it, wherein at least one sequence selected from the group of SEQ ID no. 9, 10, 11, 12, 13, 14, 15 or 16 is released through cleavage by TEV (e.g., SEQ ID no. 1 or SEQ ID no. 2) at the recognition sequence ENLYFQS (SEQ ID no. 3) or ENLYFQG (SEQ ID no. 4).

Therefore, the invention relates to an inactive form of caspase 3 and/or caspase 7 and/or caspase 8 and/or caspase 10, namely a fusion protein comprising at least one sequence selected from the group of SEQ ID no. 5, 6, 7 or 8 comprising ENLYFQS (SEQ ID no. 3) or ENLYFQG (SEQ ID no. 4), or a nucleic acid encoding it. Any other fusion proteins can be prepared in a corresponding manner (e.g., by means of an HIS-tag, and others), wherein the sample tag can be replaced by any peptide, for example, 50 to 100 amino acids.

The person skilled in the art is able to produce and design suitable fusion proteins (Ausubel et al. (ed.), (1989). Preparation of Genomic DNA from Mammalian Tissue. In: Short Protocols in Molecular Biology: A Compendium of Methods from CURRENT PROTOCOLS IN MOLECULAR BIOLOGY. John Wiley & Sons), cf. also examples.

In a further preferred embodiment of the invention the apoptosis resistance of cancer cells shall be overcome by delivering the fusion protein simultaneous with inhibitors of anti-apoptotic proteins, in particular selected from the group of Smac/DIABLO (SEQ ID no. 17) and XAF1 (SEQ ID no. 18).

Smac/DIABLO is an intracellular protein that functions to antagonize, i.e. inhibit the activity of IAPs (supra). Furthermore, Smac/DIABLO can promote the proteolytic activation of procaspases, however also the enzymatic activity of mature caspases. Upon an apoptotic stimulus Smac/DIABLO is usually released from mitochondria. Anyway, this release is often blocked in cancer cells by Bcl-2. In a further aspect of the invention the mitochondrial targeting sequence of Smac/DIABLO was removed in order to ensure a direct expression in the cytosol.

XAF1 is ubiquitously expressed in normal tissues but is present at low or undetectable levels in many cancers. It can degrade IAPs and induces Bax expression. Additionally, XAF1 can bind zinc which is known to inhibit caspases.

In a further preferred embodiment, the fusion protein according to the invention may comprise anti-apoptotic proteins, such as not limited to Smac/DIABLO (SEQ ID no. 17) or XAF1 (SEQ ID no. 18).

Just in order to release such anti-apoptotic proteins, the fusion protein may comprise one or more TEV recognition sites as explanatory depicted in FIG. 1. An appropriate example of such a fusion protein is presented in SEQ ID no. 19, wherein e.g. caspase 3, caspase 7, SMAC, XAF1 and TEV are arranged in one plasmid with inserted TEV recognition sites and linker sequences between the different proteins.

The inventive fusion protein or combination preparations and drugs can have suitable excipients and additives added to them. Examples of suitable additives and/or excipients are, e.g., physiological saline solution, stabilizers, proteinase inhibitors, nuclease inhibitors, etc.

Therefore, the invention also relates to a combination preparation or drug as described above for application or use in the treatment and/or prophylaxis of cancer or tumor diseases in humans and animals, especially mammals.

In another preferred embodiment, the inventive combination preparations or drugs are administered by means of a gene therapy process.

Gene therapy processes can be obtained, e.g., by complexing the inventive nucleic acids with liposomes. Lipid mixtures suitable for this purpose are described by Felgner, P. L. et al. (1987) Proc. Natl. Acad. Sci, USA 84, 7413; Behr, J. P. et al. (1989) Proc. Natl. Acad. Sci. USA 86, 6982; Felgner, J. H. et al. (1994) J. Biol. Chem. 269, 2550, or Gao, X. & Huang, L. (1991) Biochim. Biophys. Acta 1189, 195. When the liposomes are produced, the DNA is ionically bound to the surface of the liposomes, and in such a ratio that a positive net charge remains, and the DNA is completely complexed by the liposomes. Sterically stabilized liposomes with a polyethylene glycol (PEG) shell exhibit clearly reduced ingestion through the mononuclear phagocyte system (MPS), and also have greatly prolonged blood circulation times, reduced aggregation of PEGylated vesicles, and improved stability of the liposomal formulations. Analogous to PEG, linear and hyperbranched polyglycerol (lPG and hbPG) show excellent biocompatibility, but allow further derivatives to be formed by the addition of functional groups. Novel lipids based on hyperbranched polyglycerol, linear-hyperbranched PEG-hbPG-block copolymers and statistical PEG-PG-copolymers were produced through combined anionic polymerizations of various epoxide monomers using lipophilic initiators such as cholesterol or 1,2-bis-n-alkyl glyceryl ethers. The novel amphiphilic structures were successfully introduced into liposomal membranes using 1,2-dioleoyl-sn-glycero-3-phosphocholine (DOPC) as a colipid.

Therefore, the invention also relates to a gene therapy process involving delivery into a target cell, preferably a tumor cell, by using a vehicle.

In another embodiment, this vehicle can be selected from the group of liposomes, nano- or microparticles, viruses, lipoplexes, etc. (Gene delivery by lipoplexes and polyplexes. Tros de Ilarduya C, Sun Y, Düzgüneş N. Eur J Pharm Sci. 2010 Jun. 14; 40 (3):159-70. doi: 10.1016/j.ejps.2010.03.019. Epub 2010 Mar. 30; Efficient gene delivery by EGF-lipoplexes in vitro and in vivo, Buñuales M, Düzgüneş N, Zalba S, Garrido M J, de Ilarduya C T. Nanomedicine (Lond). 2011 January; 6 (1):89-98. doi: 10.2217/nnm.10.100; Genetic nanomedicine: gene delivery by targeted lipoplexes, Düzgüneş N, de Ilarduya C T. Methods Enzymol. 2012; 509:355-67. doi: 10.1016/B978-0-12-391858-1.00018-6).

In an especially preferred embodiment, the inventive vehicles have ligands on the surface that recognize tumor markers. Examples of such ligands are polyclonal or monoclonal antibodies or covalent binders (aptamers) that are able to bind to tumor markers.

Finally, such presenting tumor markers cannot be limited to or can encompass particularly:

Carcinoembryonic antigen (CEA), alpha fetoprotein (AFP), carbohydrate antigen 19-9 (CA19-9), cancer antigen 72-4 (CA 72-4), cancer antigen 125, cancer antigen 15-3 (CA 15-3), neuron-specific enolase (NSE), squamous cell carcinoma antigen (SCC), cytokeratin fragment (CYFRA), human chorionic gonadotropin (HCG), prostate-specific antigen (PSA), human thyroglobulin (HTG), mucin-like cancer associated antigen (MCA), etc. FIG. 2 shows examples of tumor markers and the cancers for which they are suitable.

Therefore, the invention also relates to a process for introducing an inventive drug or fusion protein, wherein an inactive form of caspase 3 and/or caspase 7 and/or caspase 8 and/or caspase 10 comprising a nucleic acid encoding SEQ ID no. 5, 6, 7 or 8, and a nucleic acid encoding tobacco etch virus protease (e.g., SEQ ID no. 1 or SEQ ID no. 2), especially an inactive form of caspase 3 and/or caspase 7 and/or caspase 8 and/or caspase 10 comprising a nucleic acid encoding a fusion protein comprising at least one sequence selected from the group of SEQ ID no. 9, 10, 11, 12, 13, 14, 15 or 16 and ENLYFQS (SEQ ID no. 3) or ENLYFQG (SEQ ID no. 4) and a nucleic acid encoding tobacco etch virus protease, i.) are introduced in at least one vehicle,
ii.) into a tumor cell and expressed there,
iii.) producing an active form of caspase 3 and/or caspase 7 and/or caspase 8 and/or caspase 10 and inducing cell death in the tumor cell.

The process can be correspondingly adapted by other previously mentioned embodiments. The inventive drugs, fusion protein, and especially their vehicles can preferably be locally administered to humans and animals, e.g., subcutaneously administered. Of course, the invention comprises all applications in tumor treatment.

As defined in this invention, the term "functional variant" is understood to mean polypeptides or nucleic acids that are functionally related with the inventive peptide. The term "variants" is also understood to mean allelic variants or polypeptides and nucleic acids that are derived from other organisms, cells, or tissues.

More broadly, it is also understood to mean polypeptides or nucleic acids that have a sequence homology, especially a sequence identity, of about 70%, preferably about 80%, especially preferably about 90%, most preferably about 95% with the designated SEQ ID.

This also includes polypeptide deletion in the range of about 1-50, preferably about 1-30, especially preferably about 1-15, most preferably about 1-6 amino acids. For example, the first amino acid can lack methionine, without substantially changing the function of the polypeptide.

In addition, this also includes fusion proteins that contain the above-described inventive polypeptides, the fusion proteins themselves already having the function of the respective SEQ ID or only being able to acquire the specific function after elimination of the fusion moiety. Above all, this includes fusion proteins whose component especially of non-human sequences is about 1-50, preferably about 1-30 amino acids. Examples of non-human peptide sequences are prokaryotic peptide sequences, e.g., from *E. coli* galactosidase or [those with] a so-called histidine tag, e.g., a Met-Ala-His6-Tag. An especially advantageous application for which fusion proteins with a so-called histidine tag are suitable is to purify the expressed protein through metal ion-containing columns, for example through a $Ni^{2+}$-NTA column. Here "NTA" stands for the chelating agent nitrilotriacetic acid (Qiagen GmbH, Hilden).

Especially the mentioned parts of the polypeptide can also be synthesized using classical peptide synthesis (Merrifield method). They are especially suitable for obtaining antisera, which can be used to search through suitable gene expression libraries to achieve other functional variants of the inventive polypeptides.

In a preferred embodiment, the inventive nucleic acid previously mentioned in each case is a DNA, cDNA, or RNA, preferably a double-stranded DNA, however a PNA or something similar is also conceivable.

The inventive nucleic acids can also be introduced into the tumor cell by means of (expression) vectors, for example, by means of the vector pcDNA™3.1 (Invitrogen) with a constitutive CMV promoter, etc.

As defined in this invention, the terms tumor, cancer, cancer cells, and tumor cells should be read as synonyms, and comprise every benign or malignant tumor, especially a growth with a locally circumscribed increase in tissue volume, comprising every localized swelling due to edema, acute and chronic inflammation, aneurysmal enlargement (pulsating tumor) etc., and also inflammatory organ swelling (e.g., as in the case of a so-called splenic tumor) as well as a tissue neoplasm (growth, blastoma, neoplasia) in the form of a spontaneous, autonomous and irreversible excessive growth of the body's own tissue, disinhibited to different extents, which is, as a rule, connected with loss of specific cell and tissue functions of different severity (see Pschyrembel, (266st edition) 2014, de Gruyter, Berlin).

EXAMPLES AND FIGURES

These examples serve exclusively to explain the invention, without limiting the invention to these examples.

Example

Example 1

Experimental Data

Genes coding for caspase 3, caspase 7, caspase 8, caspase 10, Smac/DIABOLO and XAF1 were cloned into a commercially available EGFP plasmid (pEGFP-N1). The fluorescent protein EGFP allows the visualization of the proteins by fluorescence microscopy. TEV recognition sites (ENLYFQ/S or ENLYFQ/A) were inserted between the different proteins. TEV recognition sites are flanked by glycin/alanine linker sequences to provide structural flexibility and thereby enhance cleavage efficiency. The natural cleavage site of the caspases was exchanged by TEV recognition sites, e.g., as depicted in SEQ ID No. 5-8.

The resulting plasmids were transfected into different cells lines e.g. HEK and WM35 (melanoma) using Fugene6 transfection reagent (Promega). One day before transfection, 1×104 cells were seeded in each well of a 96-well plate leading to a confluence of approximately 80% on the day of transfection. FuGene6 transfection reagent was added to a tube containing Opti-MEM I (Invitrogen, Karlsruhe) and incubated for 5 minutes. A 3:1 reagent to DNA ratio was used. 100 ng of plasmid DNA were added to the FuGene 6 transfection reagent/medium and mixed immediately. After an incubation for 15 minutes at room temperature 8 μL of the transfection sample was added to the cell culture medium. Cells were analyzed by fluorescence microscopy.

Apoptosis is evidenced by rounding and retraction of pseudopodia, plasma membrane rupture and the formation of apoptotic bodies.

HEK Cells

Apoptosis is induced by Cas3-TEV-EGFP, Cas7-TEV-EGFP, Cas3-Cas7-TEV-EGFP, XAF1-Smac-TEV-EGFP and Cas3-Cas7-Smac-TEV-EGFP Smac-TEV-EGFP and XAF1-TEV-EGFP are not able to induce apoptosis in healthy cells WM35 Cells The single protein TEV constructs can partly induce apoptosis A better apoptosis induction is reached by the combinatory constructs Cas3-Cas7-TEV-EGFP, XAF1-Smac-TEV-EGFP and Cas3-Cas7-Smac-TEV-EGFP

The invention claimed is:

1. A fusion protein comprising
   (a) at least one variant caspase;
   (b) at least one inhibitor of anti-apoptotic proteins; and
   (c) a tobacco etch virus (TEV) protease,
   wherein:
   (i) the at least one variant caspase, the at least one inhibitor of anti-apoptotic proteins and the TEV protease are all separated by recognition sites for the TEV protease, so they can be released from each other upon cleavage by the TEV protease;
   (ii) the variant caspase comprises a TEV recognition site, so that upon cleavage by the TEV protease two fragments of the caspase are released,
      wherein the at least one variant caspase is selected from the group consisting of:
   variant caspase 3 having SEQ ID NO: 5, from which fragments of SEQ ID NOS: 9 and 10 are released upon cleavage by the TEV protease;
   variant caspase 7 having SEQ ID NO: 6, from which the fragments of SEQ ID NOs: 11 and 12 are released upon cleavage by the TEV protease;
   variant caspase 8 having SEQ ID NO: 7, from which the fragments of SEQ ID NOs: 13 and 14 are released upon cleavage by the TEV protease; and
   variant caspase 10 having SEQ ID NO: 8, from which the fragments of SEQ ID NOs: 15 and 16 are released upon cleavage by the TEV protease,
   (iii) the inhibitor of anti-apoptotic proteins is selected from the group consisting of second mitochondria-derived activator of caspase/direct inhibitor of apoptosis-binding protein with low pI (Smac/DIABLO) comprising SEQ ID NO:17 and X-linked inhibitor of apoptosis-associated factor-1 (XAF1) comprising SEQ ID NO:18; and
   (iv) the recognition sites for the TEV protease separating the at least one variant caspase, the at least one inhibitor and the TEV protease are selected from the group consisting of ENKYFQS (SEQ ID NO: 3) and ENLYFQG (SEQ ID NO: 4).

2. The fusion protein according to claim 1, wherein the fusion protein comprises SEQ ID NO: 19.

3. The fusion protein according to claim 1, wherein the TEV protease comprises SEQ ID NO: 1 or 2.

4. A nucleic acid encoding the fusion protein according to claim 1.

5. A composition comprising the nucleic acid according to claim 4 and optionally an excipient or an additive.

6. The nucleic acid according to claim 4, wherein the composition further comprises a vehicle.

7. The nucleic acid according to claim 6, wherein the vehicle is selected from the group consisting of liposomes, nanoparticles, microparticles, viruses, and lipoplexes.

8. The nucleic acid according to claim 6, wherein the vehicle contains ligands that recognize tumor markers.

9. A process for introducing a nucleic acid encoding the fusion protein according to claim 1 into a tumor cell comprising:
   1) combining the nucleic acid encoding the fusion protein according to claim 1 with a vehicle to produce a nucleic acid composition; and
   2) administering the nucleic composition of step 1) to the tumor cell,
   wherein the nucleic acid composition of step 1) produces an active form of caspase 3 and/or caspase 7 and/or caspase 8 and/or caspase 10 and induces cell death in the tumor cell.

10. The nucleic acid according to claim 8, wherein the tumor markers are selected from the group of carcinoembryonic antigen (CEA), alpha fetoprotein (AFP), carbohydrate antigen 19-9 (CA19-9), cancer antigen 72-4 (CA 72-4), cancer antigen 125, cancer antigen 15-3 (CA 15-3), neuron-specific enolase (NSE), squamous cell carcinoma antigen (SCC), cytokeratin fragment (CYFRA), human chorionic gonadotropin (HCG), prostate-specific antigen (PSA), human thyroglobulin (HTG), mucin-like cancer associated antigen (MCA).

11. The composition according to claim 1, wherein the inhibitor of anti-apoptotic proteins is Smac/DIABLO and XAF1.

12. A method of treating a cancer or tumor disease in a subject in need thereof, the method comprising administering a therapeutically effective amount of the fusion protein according to claim 1.

13. A method of treating a cancer or tumor disease in a subject in need thereof, the method comprising administering a therapeutically effective amount of the nucleic acid according to claim 4.

14. A method of treating a cancer or tumor disease in a subject in need thereof, the method comprising administering a therapeutically effective amount of the composition according to claim 5.

* * * * *

SEQUENCE LISTING

<160> NUMBER OF SEQ ID NOS: 19

Figure 1:
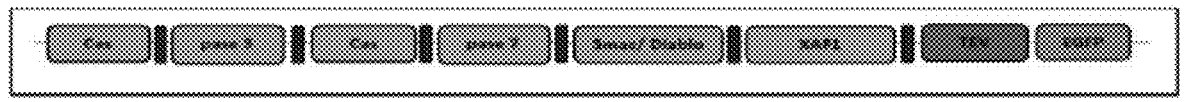
FIG. 1 describes embodiments of the fusion peptides.
Figure 2:
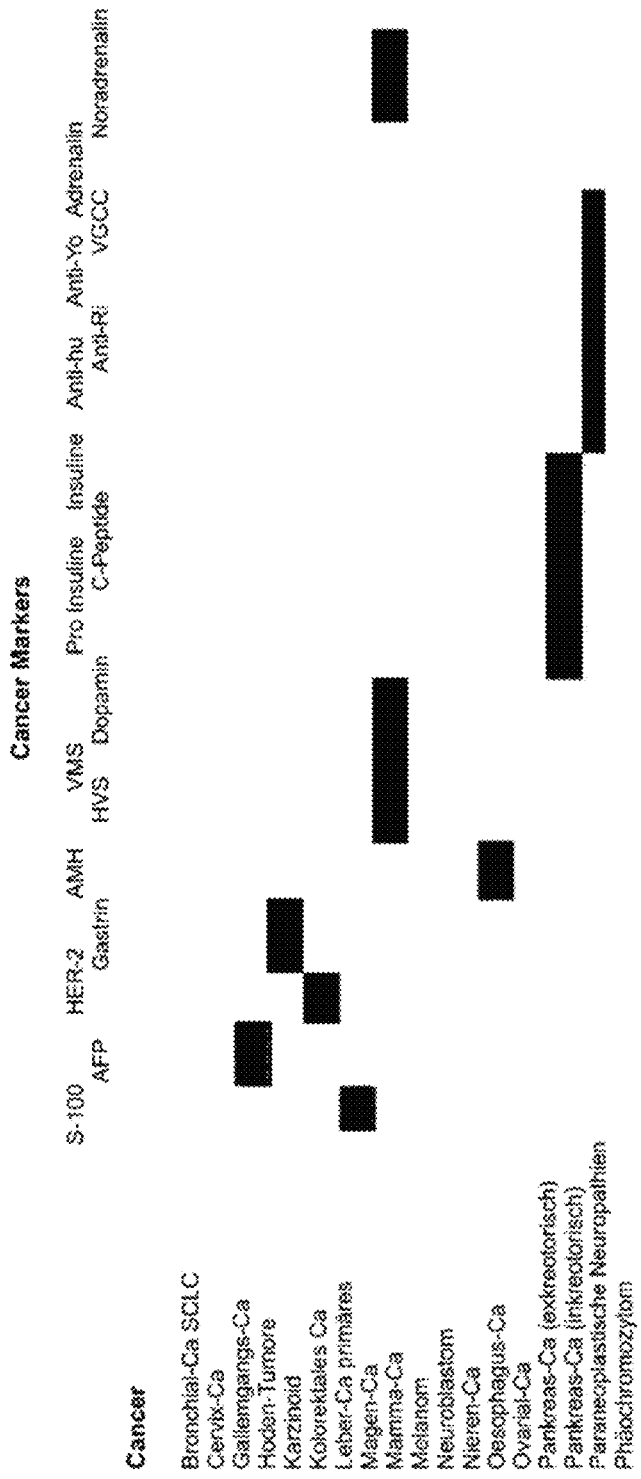
FIG. 2 shows tumor markers for certain cancer diseases.
Figure 2:
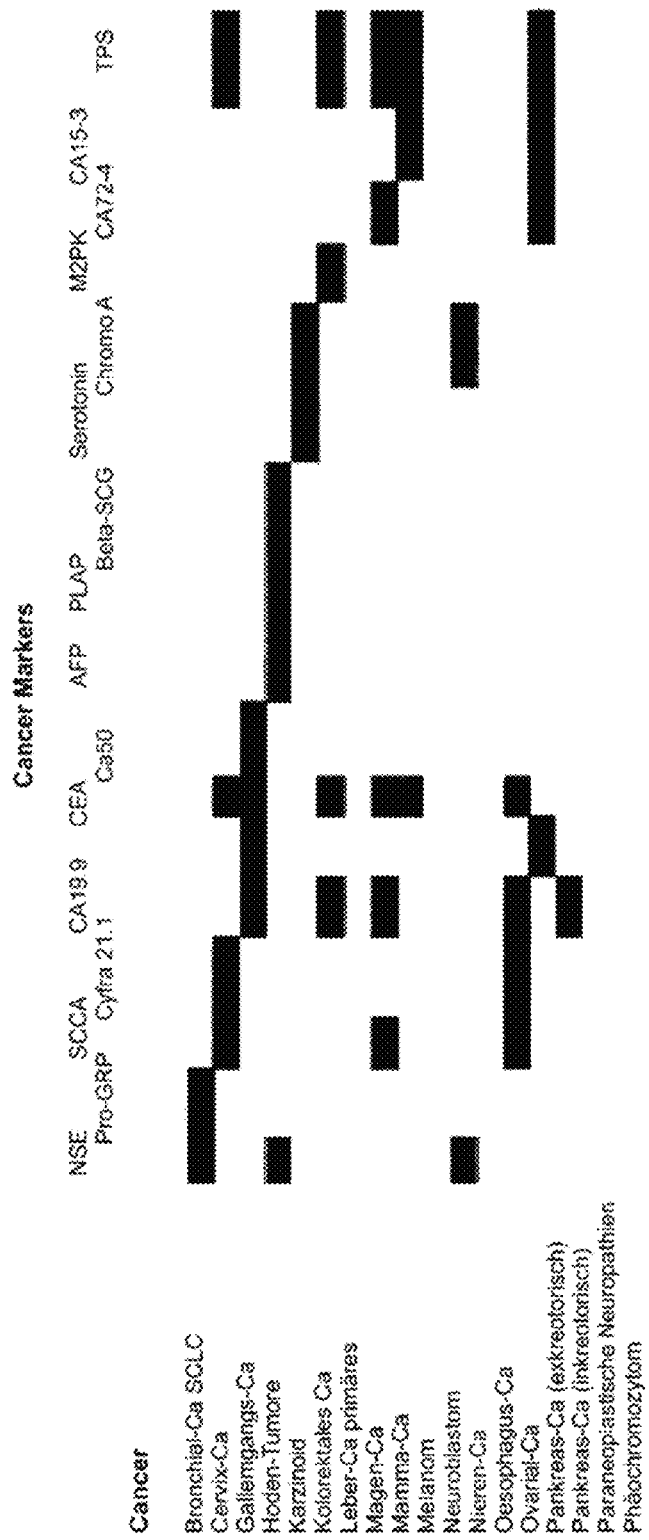

<210> SEQ ID NO 1
<211> LENGTH: 243
<212> TYPE: PRT
<213> ORGANISM: tobacco etch virus

<400> SEQUENCE: 1

Met Gly Glu Ser Leu Phe Lys Gly Pro Arg Asp Tyr Asn Pro Ile Ser
1               5                   10                  15

Ser Thr Ile Cys His Leu Thr Asn Glu Ser Asp Gly His Thr Thr Ser
            20                  25                  30

Leu Tyr Gly Ile Gly Phe Gly Pro Phe Ile Ile Thr Asn Lys His Leu
        35                  40                  45

Phe Arg Arg Asn Asn Gly Thr Leu Leu Val Gln Ser Leu His Gly Val
    50                  55                  60

Phe Lys Val Lys Asp Thr Thr Leu Gln Gln His Leu Ile Asp Gly
65                  70                  75                  80

Arg Asp Met Met Ile Ile Arg Met Pro Lys Asp Phe Pro Pro Phe Pro
                85                  90                  95

Gln Lys Leu Lys Phe Arg Glu Pro Gln Arg Glu Glu Arg Ile Cys Leu
            100                 105                 110

Val Thr Thr Asn Phe Gln Ala Lys Ser Met Ser Ser Met Val Ser Asp
            115                 120                 125

Thr Ser Cys Thr Phe Pro Ser Ser Asp Gly Ile Phe Trp Lys His Trp
        130                 135                 140

Ile Gln Thr Lys Asp Gly Gln Cys Gly Ser Pro Leu Val Ser Thr Arg
145                 150                 155                 160

Asp Gly Phe Ile Val Gly Ile His Ser Ala Ser Asn Phe Thr Asn Thr
                165                 170                 175

Asn Asn Tyr Phe Thr Ser Val Pro Lys Asn Phe Met Glu Leu Leu Thr
            180                 185                 190

Asn Gln Glu Ala Gln Gln Trp Val Ser Gly Trp Arg Leu Asn Ala Asp
            195                 200                 205

Ser Val Leu Trp Gly Gly His Lys Val Phe Met Val Lys Pro Glu Glu
        210                 215                 220

Pro Phe Gln Pro Val Lys Glu Ala Thr Gln Leu Met Asn Glu Leu Val
225                 230                 235                 240

Tyr Ser Gln

<210> SEQ ID NO 2
<211> LENGTH: 262
<212> TYPE: PRT
<213> ORGANISM: tobacco etch virus

<400> SEQUENCE: 2

Met Lys His His His His His His Pro Met Ser Gly Leu Val Pro Arg
1               5                   10                  15

Gly Ser Ala Met Gly Glu Ser Leu Phe Lys Gly Pro Arg Asp Tyr Asn
            20                  25                  30

Pro Ile Ser Ser Thr Ile Cys His Leu Thr Asn Glu Ser Asp Gly His
        35                  40                  45

Thr Thr Ser Leu Tyr Gly Ile Gly Phe Gly Pro Phe Ile Ile Thr Asn
    50                  55                  60

Lys His Leu Phe Arg Arg Asn Asn Gly Thr Leu Leu Val Gln Ser Leu
65                  70                  75                  80

```
His Gly Val Phe Lys Val Lys Asp Thr Thr Thr Leu Gln Gln His Leu
                85                  90                  95

Ile Asp Gly Arg Asp Met Met Ile Ile Arg Met Pro Lys Asp Phe Pro
            100                 105                 110

Pro Phe Pro Gln Lys Leu Lys Phe Arg Glu Pro Gln Arg Glu Glu Arg
        115                 120                 125

Ile Cys Leu Val Thr Thr Asn Phe Gln Ala Lys Ser Met Ser Ser Met
    130                 135                 140

Val Ser Asp Thr Ser Cys Thr Phe Pro Ser Ser Asp Gly Ile Phe Trp
145                 150                 155                 160

Lys His Trp Ile Gln Thr Lys Asp Gly Gln Cys Gly Ser Pro Leu Val
                165                 170                 175

Ser Thr Arg Asp Gly Phe Ile Val Gly Ile His Ser Ala Ser Asn Phe
            180                 185                 190

Thr Asn Thr Asn Asn Tyr Phe Thr Ser Val Pro Lys Asn Phe Met Glu
        195                 200                 205

Leu Leu Thr Asn Gln Glu Ala Gln Gln Trp Val Ser Gly Trp Arg Leu
    210                 215                 220

Asn Ala Asp Ser Val Leu Trp Gly Gly His Lys Val Phe Met Val Lys
225                 230                 235                 240

Pro Glu Glu Pro Phe Gln Pro Val Lys Glu Ala Thr Gln Leu Met Asn
                245                 250                 255

Glu Leu Val Tyr Ser Gln
            260

<210> SEQ ID NO 3
<211> LENGTH: 7
<212> TYPE: PRT
<213> ORGANISM: Artificial sequence
<220> FEATURE:
<223> OTHER INFORMATION: TEV recognition site

<400> SEQUENCE: 3

Glu Asn Leu Tyr Phe Gln Ser
1               5

<210> SEQ ID NO 4
<211> LENGTH: 7
<212> TYPE: PRT
<213> ORGANISM: Artificial sequence
<220> FEATURE:
<223> OTHER INFORMATION: TEV recognition site

<400> SEQUENCE: 4

Glu Asn Leu Tyr Phe Gln Gly
1               5

<210> SEQ ID NO 5
<211> LENGTH: 272
<212> TYPE: PRT
<213> ORGANISM: Artificial sequence
<220> FEATURE:
<223> OTHER INFORMATION: casapase 3 with TEV recognition site

<400> SEQUENCE: 5

Met Glu Asn Thr Glu Asn Ser Val Asp Ser Lys Ser Ile Lys Asn Leu
1               5                   10                  15

Glu Pro Lys Ile Ile His Gly Ser Glu Ser Met Asp Ser Gly Ile Ser
            20                  25                  30
```

Leu Asp Asn Ser Tyr Lys Met Asp Tyr Pro Glu Met Gly Leu Cys Ile
            35                  40                  45

Ile Ile Met Thr Ser Arg Ser Gly Thr Asp Val Asp Ala Ala Asn Leu
 50                  55                  60

Arg Glu Thr Phe Arg Asn Leu Lys Tyr Glu Val Arg Asn Lys Asn Asp
 65                  70                  75                  80

Leu Thr Arg Glu Glu Ile Val Glu Leu Met Arg Asp Val Ser Lys Glu
            85                  90                  95

Asp His Ser Lys Arg Ser Ser Phe Val Cys Val Leu Leu Ser His Gly
            100                 105                 110

Glu Glu Gly Ile Ile Phe Gly Thr Asn Gly Pro Val Asp Leu Lys Lys
            115                 120                 125

Ile Thr Asn Phe Phe Arg Gly Asp Arg Cys Arg Ser Leu Thr Gly Lys
            130                 135                 140

Pro Lys Leu Phe Ile Ile Gln Ala Cys Arg Cys Thr Glu Leu Asp Cys
145                 150                 155                 160

Gly Ile Glu Thr Glu Asn Leu Tyr Phe Gln Ser Gly Val Asp Asp Asp
            165                 170                 175

Met Ala Cys His Lys Ile Pro Val Glu Ala Asp Phe Leu Tyr Ala Tyr
            180                 185                 190

Ser Thr Ala Pro Gly Tyr Tyr Ser Trp Arg Asn Ser Lys Asp Gly Ser
            195                 200                 205

Trp Phe Ile Gln Ser Leu Cys Ala Met Leu Lys Gln Tyr Ala Asp Lys
            210                 215                 220

Leu Glu Phe Met His Ile Leu Thr Arg Val Asn Arg Lys Val Ala Thr
225                 230                 235                 240

Glu Phe Glu Ser Phe Ser Phe Asp Ala Thr Phe His Ala Lys Lys Gln
            245                 250                 255

Ile Pro Cys Ile Val Ser Met Leu Thr Lys Glu Leu Tyr Phe Tyr His
            260                 265                 270

<210> SEQ ID NO 6
<211> LENGTH: 308
<212> TYPE: PRT
<213> ORGANISM: Artificial sequence
<220> FEATURE:
<223> OTHER INFORMATION: caspase 7 with TEV recognition site

<400> SEQUENCE: 6

Ala Asp Asp Gln Gly Cys Ile Glu Glu Gln Gly Val Glu Asp Ser Ala
 1                   5                  10                  15

Asn Glu Asp Ser Val Asp Ala Lys Pro Asp Arg Ser Ser Phe Val Pro
            20                  25                  30

Ser Leu Phe Ser Lys Lys Lys Asn Val Thr Met Arg Ser Ile Lys
            35                  40                  45

Thr Thr Arg Asp Arg Val Pro Thr Tyr Gln Tyr Asn Met Asn Phe Glu
 50                  55                  60

Lys Leu Gly Lys Cys Ile Ile Ile Asn Asn Lys Asn Phe Asp Lys Val
 65                  70                  75                  80

Thr Gly Met Gly Val Arg Asn Gly Thr Asp Lys Asp Ala Glu Ala Leu
            85                  90                  95

Phe Lys Cys Phe Arg Ser Leu Gly Phe Asp Val Ile Val Tyr Asn Asp
            100                 105                 110

Cys Ser Cys Ala Lys Met Gln Asp Leu Leu Lys Lys Ala Ser Glu Glu
            115                 120                 125

```
Asp His Thr Asn Ala Ala Cys Phe Ala Cys Ile Leu Leu Ser His Gly
    130                 135                 140

Glu Glu Asn Val Ile Tyr Gly Lys Asp Gly Val Thr Pro Ile Lys Asp
145                 150                 155                 160

Leu Thr Ala His Phe Arg Gly Asp Arg Cys Lys Thr Leu Leu Glu Lys
                165                 170                 175

Pro Lys Leu Phe Phe Ile Gln Ala Cys Arg Gly Thr Glu Leu Asp Asp
            180                 185                 190

Gly Ile Gln Ala Glu Asn Leu Tyr Phe Gln Ser Gly Pro Ile Asn Asp
        195                 200                 205

Thr Asp Ala Asn Pro Arg Tyr Lys Ile Pro Val Glu Ala Asp Phe Leu
210                 215                 220

Phe Ala Tyr Ser Thr Val Pro Gly Tyr Tyr Ser Trp Arg Ser Pro Gly
225                 230                 235                 240

Arg Gly Ser Trp Phe Val Gln Ala Leu Cys Ser Ile Leu Glu Glu His
                245                 250                 255

Gly Lys Asp Leu Glu Ile Met Gln Ile Leu Thr Arg Val Asn Asp Arg
            260                 265                 270

Val Ala Arg His Phe Glu Ser Gln Ser Asp Asp Pro His Phe His Glu
275                 280                 285

Lys Lys Gln Ile Pro Cys Val Val Ser Met Leu Thr Lys Glu Leu Tyr
290                 295                 300

Gly Phe Ser Gln
305

<210> SEQ ID NO 7
<211> LENGTH: 265
<212> TYPE: PRT
<213> ORGANISM: Artificial sequence
<220> FEATURE:
<223> OTHER INFORMATION: caspase 8 with TEV recognition site

<400> SEQUENCE: 7

Met Asp Ser Glu Ser Gln Thr Leu Asp Lys Val Tyr Gln Met Lys Ser
1               5                   10                  15

Lys Pro Arg Gly Tyr Cys Leu Ile Ile Asn Asn His Asn Phe Ala Lys
            20                  25                  30

Ala Arg Glu Lys Val Pro Lys Leu His Ser Ile Arg Asp Arg Asn Gly
        35                  40                  45

Thr His Leu Asp Ala Gly Ala Leu Thr Thr Thr Phe Glu Glu Leu His
    50                  55                  60

Phe Glu Ile Lys Pro His Asp Asp Cys Thr Val Glu Gln Ile Tyr Glu
65                  70                  75                  80

Ile Leu Lys Ile Tyr Gln Leu Met Asp His Ser Asn Met Asp Cys Phe
                85                  90                  95

Ile Cys Cys Ile Leu Ser His Gly Asp Lys Gly Ile Ile Tyr Gly Thr
            100                 105                 110

Asp Gly Gln Glu Ala Pro Ile Tyr Glu Leu Thr Ser Gln Phe Thr Gly
        115                 120                 125

Leu Lys Cys Pro Ser Leu Ala Gly Lys Pro Lys Val Phe Phe Ile Gln
    130                 135                 140

Ala Cys Gln Gly Asp Asn Tyr Gln Lys Gly Ile Pro Val Glu Thr Asp
145                 150                 155                 160

Ser Glu Asn Leu Tyr Phe Gln Gly Met Asp Leu Ser Ser Pro Gln Thr
                165                 170                 175
```

```
Arg Tyr Ile Pro Asp Glu Ala Asp Phe Leu Leu Gly Met Ala Thr Val
                180                 185                 190

Asn Asn Cys Val Ser Tyr Arg Asn Pro Ala Glu Gly Thr Trp Tyr Ile
            195                 200                 205

Gln Ser Leu Cys Gln Ser Leu Arg Glu Arg Cys Pro Arg Gly Asp Asp
        210                 215                 220

Ile Leu Thr Ile Leu Thr Glu Val Asn Tyr Glu Val Ser Asn Lys Asp
225                 230                 235                 240

Asp Lys Lys Asn Met Gly Lys Gln Met Pro Gln Pro Thr Phe Thr Leu
                245                 250                 255

Arg Lys Lys Leu Val Phe Pro Ser Asp
                260                 265

<210> SEQ ID NO 8
<211> LENGTH: 305
<212> TYPE: PRT
<213> ORGANISM: Artificial sequence
<220> FEATURE:
<223> OTHER INFORMATION: casapase 10 with TEV recognition site

<400> SEQUENCE: 8

Met Asp Val Lys Thr Phe Leu Glu Ala Leu Pro Gln Glu Ser Trp Gln
1               5                   10                  15

Asn Lys His Ala Gly Ser Asn Gly Asn Arg Ala Thr Asn Gly Ala Pro
            20                  25                  30

Ser Leu Val Ser Arg Gly Met Gln Gly Ala Ser Ala Asn Thr Leu Asn
        35                  40                  45

Ser Glu Thr Ser Thr Lys Arg Ala Ala Val Tyr Arg Met Asn Arg Asn
50                  55                  60

His Arg Gly Leu Cys Val Ile Val Asn Asn His Ser Phe Thr Ser Leu
65                  70                  75                  80

Lys Asp Arg Gln Gly Thr His Lys Asp Ala Glu Ile Leu Ser His Val
                85                  90                  95

Phe Gln Trp Leu Gly Phe Thr Val His Ile His Asn Asn Val Thr Lys
            100                 105                 110

Val Glu Met Glu Met Val Leu Gln Lys Gln Lys Cys Asn Pro Ala His
        115                 120                 125

Ala Asp Gly Asp Cys Phe Val Phe Cys Ile Leu Thr His Gly Arg Phe
130                 135                 140

Gly Ala Val Tyr Ser Ser Asp Glu Ala Leu Ile Pro Ile Arg Glu Ile
145                 150                 155                 160

Met Ser His Phe Thr Ala Leu Gln Cys Pro Arg Leu Ala Glu Lys Pro
                165                 170                 175

Lys Leu Phe Phe Ile Gln Ala Cys Gln Gly Glu Glu Ile Gln Pro Ser
            180                 185                 190

Val Ser Ile Glu Ala Glu Asn Leu Tyr Phe Gln Gly Gln Ala Pro Thr
        195                 200                 205

Ser Leu Gln Asp Ser Ile Pro Ala Glu Ala Asp Phe Leu Leu Gly Leu
        210                 215                 220

Ala Thr Val Pro Gly Tyr Val Ser Phe Arg His Val Glu Glu Gly Ser
225                 230                 235                 240

Trp Tyr Ile Gln Ser Leu Cys Asn His Leu Lys Lys Leu Val Pro Arg
                245                 250                 255

Met Leu Lys Phe Leu Glu Lys Thr Met Glu Ile Arg Gly Arg Lys Arg
            260                 265                 270
```

```
Thr Val Trp Gly Ala Lys Gln Ile Ser Ala Thr Ser Leu Pro Thr Ala
            275                 280                 285

Ile Ser Ala Gln Thr Pro Arg Pro Met Arg Trp Ser Ser Val
            290                 295                 300

Ser
305

<210> SEQ ID NO 9
<211> LENGTH: 170
<212> TYPE: PRT
<213> ORGANISM: Artificial sequence
<220> FEATURE:
<223> OTHER INFORMATION: Cleaved Part of caspase 3 by TEV

<400> SEQUENCE: 9

Met Glu Asn Thr Glu Asn Ser Val Asp Ser Lys Ser Ile Lys Asn Leu
1               5                   10                  15

Glu Pro Lys Ile Ile His Gly Ser Glu Ser Met Asp Ser Gly Ile Ser
            20                  25                  30

Leu Asp Asn Ser Tyr Lys Met Asp Tyr Pro Glu Met Gly Leu Cys Ile
            35                  40                  45

Ile Ile Met Thr Ser Arg Ser Gly Thr Asp Val Asp Ala Ala Asn Leu
50                  55                  60

Arg Glu Thr Phe Arg Asn Leu Lys Tyr Glu Val Arg Asn Lys Asn Asp
65                  70                  75                  80

Leu Thr Arg Glu Glu Ile Val Glu Leu Met Arg Asp Val Ser Lys Glu
            85                  90                  95

Asp His Ser Lys Arg Ser Ser Phe Val Cys Val Leu Leu Ser His Gly
            100                 105                 110

Glu Glu Gly Ile Ile Phe Gly Thr Asn Gly Pro Val Asp Leu Lys Lys
            115                 120                 125

Ile Thr Asn Phe Phe Arg Gly Asp Arg Cys Arg Ser Leu Thr Gly Lys
            130                 135                 140

Pro Lys Leu Phe Ile Ile Gln Ala Cys Arg Cys Thr Glu Leu Asp Cys
145                 150                 155                 160

Gly Ile Glu Thr Glu Asn Leu Tyr Phe Gln
            165                 170

<210> SEQ ID NO 10
<211> LENGTH: 102
<212> TYPE: PRT
<213> ORGANISM: Artificial sequence
<220> FEATURE:
<223> OTHER INFORMATION: Cleaved part of caspase 3 by TEV

<400> SEQUENCE: 10

Ser Gly Val Asp Asp Asp Met Ala Cys His Lys Ile Pro Val Glu Ala
1               5                   10                  15

Asp Phe Leu Tyr Ala Tyr Ser Thr Ala Pro Gly Tyr Tyr Ser Trp Arg
            20                  25                  30

Asn Ser Lys Asp Gly Ser Trp Phe Ile Gln Ser Leu Cys Ala Met Leu
            35                  40                  45

Lys Gln Tyr Ala Asp Lys Leu Glu Phe Met His Ile Leu Thr Arg Val
            50                  55                  60

Asn Arg Lys Val Ala Thr Glu Phe Glu Ser Phe Ser Phe Asp Ala Thr
65                  70                  75                  80

Phe His Ala Lys Lys Gln Ile Pro Cys Ile Val Ser Met Leu Thr Lys
            85                  90                  95
```

Glu Leu Tyr Phe Tyr His
            100

<210> SEQ ID NO 11
<211> LENGTH: 202
<212> TYPE: PRT
<213> ORGANISM: Artificial sequence
<220> FEATURE:
<223> OTHER INFORMATION: Cleaved part of caspase 7 by TEV

<400> SEQUENCE: 11

Ala Asp Asp Gln Gly Cys Ile Glu Glu Gln Gly Val Glu Asp Ser Ala
1               5                   10                  15

Asn Glu Asp Ser Val Asp Ala Lys Pro Asp Arg Ser Ser Phe Val Pro
            20                  25                  30

Ser Leu Phe Ser Lys Lys Lys Asn Val Thr Met Arg Ser Ile Lys
        35                  40                  45

Thr Thr Arg Asp Arg Val Pro Thr Tyr Gln Tyr Asn Met Asn Phe Glu
    50                  55                  60

Lys Leu Gly Lys Cys Ile Ile Ile Asn Asn Lys Asn Phe Asp Lys Val
65                  70                  75                  80

Thr Gly Met Gly Val Arg Asn Gly Thr Asp Lys Asp Ala Glu Ala Leu
                85                  90                  95

Phe Lys Cys Phe Arg Ser Leu Gly Phe Asp Val Ile Val Tyr Asn Asp
            100                 105                 110

Cys Ser Cys Ala Lys Met Gln Asp Leu Leu Lys Lys Ala Ser Glu Glu
        115                 120                 125

Asp His Thr Asn Ala Ala Cys Phe Ala Cys Ile Leu Leu Ser His Gly
    130                 135                 140

Glu Glu Asn Val Ile Tyr Gly Lys Asp Gly Val Thr Pro Ile Lys Asp
145                 150                 155                 160

Leu Thr Ala His Phe Arg Gly Asp Arg Cys Lys Thr Leu Leu Glu Lys
                165                 170                 175

Pro Lys Leu Phe Phe Ile Gln Ala Cys Arg Gly Thr Glu Leu Asp Asp
            180                 185                 190

Gly Ile Gln Ala Glu Asn Leu Tyr Phe Gln
        195                 200

<210> SEQ ID NO 12
<211> LENGTH: 106
<212> TYPE: PRT
<213> ORGANISM: Artificial sequence
<220> FEATURE:
<223> OTHER INFORMATION: Cleaved part of caspase 7 by TEV

<400> SEQUENCE: 12

Ser Gly Pro Ile Asn Asp Thr Asp Ala Asn Pro Arg Tyr Lys Ile Pro
1               5                   10                  15

Val Glu Ala Asp Phe Leu Phe Ala Tyr Ser Thr Val Pro Gly Tyr Tyr
            20                  25                  30

Ser Trp Arg Ser Pro Gly Arg Gly Ser Trp Phe Val Gln Ala Leu Cys
        35                  40                  45

Ser Ile Leu Glu Glu His Gly Lys Asp Leu Glu Ile Met Gln Ile Leu
    50                  55                  60

Thr Arg Val Asn Asp Arg Val Ala Arg His Phe Glu Ser Gln Ser Asp
65                  70                  75                  80

Asp Pro His Phe His Glu Lys Lys Gln Ile Pro Cys Val Val Ser Met

```
                    85                  90                  95

Leu Thr Lys Glu Leu Tyr Gly Phe Ser Gln
            100                 105

<210> SEQ ID NO 13
<211> LENGTH: 167
<212> TYPE: PRT
<213> ORGANISM: Artificial sequence
<220> FEATURE:
<223> OTHER INFORMATION: Cleaved part of caspase 8 by TEV

<400> SEQUENCE: 13

Met Asp Ser Glu Ser Gln Thr Leu Asp Lys Val Tyr Gln Met Lys Ser
1               5                   10                  15

Lys Pro Arg Gly Tyr Cys Leu Ile Ile Asn Asn His Asn Phe Ala Lys
            20                  25                  30

Ala Arg Glu Lys Val Pro Lys Leu His Ser Ile Arg Asp Arg Asn Gly
        35                  40                  45

Thr His Leu Asp Ala Gly Ala Leu Thr Thr Thr Phe Glu Glu Leu His
    50                  55                  60

Phe Glu Ile Lys Pro His Asp Asp Cys Thr Val Glu Gln Ile Tyr Glu
65                  70                  75                  80

Ile Leu Lys Ile Tyr Gln Leu Met Asp His Ser Asn Met Asp Cys Phe
                85                  90                  95

Ile Cys Cys Ile Leu Ser His Gly Asp Lys Gly Ile Ile Tyr Gly Thr
            100                 105                 110

Asp Gly Gln Glu Ala Pro Ile Tyr Glu Leu Thr Ser Gln Phe Thr Gly
        115                 120                 125

Leu Lys Cys Pro Ser Leu Ala Gly Lys Pro Lys Val Phe Phe Ile Gln
    130                 135                 140

Ala Cys Gln Gly Asp Asn Tyr Gln Lys Gly Ile Pro Val Glu Thr Asp
145                 150                 155                 160

Ser Glu Asn Leu Tyr Phe Gln
                165

<210> SEQ ID NO 14
<211> LENGTH: 98
<212> TYPE: PRT
<213> ORGANISM: Artificial sequence
<220> FEATURE:
<223> OTHER INFORMATION: Cleaved part of caspase 8 by TEV

<400> SEQUENCE: 14

Gly Met Asp Leu Ser Ser Pro Gln Thr Arg Tyr Ile Pro Asp Glu Ala
1               5                   10                  15

Asp Phe Leu Leu Gly Met Ala Thr Val Asn Asn Cys Val Ser Tyr Arg
            20                  25                  30

Asn Pro Ala Glu Gly Thr Trp Tyr Ile Gln Ser Leu Cys Gln Ser Leu
        35                  40                  45

Arg Glu Arg Cys Pro Arg Gly Asp Asp Ile Leu Thr Ile Leu Thr Glu
    50                  55                  60

Val Asn Tyr Glu Val Ser Asn Lys Asp Asp Lys Lys Asn Met Gly Lys
65                  70                  75                  80

Gln Met Pro Gln Pro Thr Phe Thr Leu Arg Lys Lys Leu Val Phe Pro
                85                  90                  95

Ser Asp
```

<210> SEQ ID NO 15
<211> LENGTH: 203
<212> TYPE: PRT
<213> ORGANISM: Artificial sequence
<220> FEATURE:
<223> OTHER INFORMATION: Cleaved part of caspase 10 by TEV

<400> SEQUENCE: 15

Met Asp Val Lys Thr Phe Leu Glu Ala Leu Pro Gln Glu Ser Trp Gln
1               5                   10                  15

Asn Lys His Ala Gly Ser Asn Gly Arg Ala Thr Asn Gly Ala Pro
            20                  25                  30

Ser Leu Val Ser Arg Gly Met Gln Gly Ala Ser Ala Asn Thr Leu Asn
        35                  40                  45

Ser Glu Thr Ser Thr Lys Arg Ala Ala Val Tyr Arg Met Asn Arg Asn
    50                  55                  60

His Arg Gly Leu Cys Val Ile Val Asn Asn His Ser Phe Thr Ser Leu
65                  70                  75                  80

Lys Asp Arg Gln Gly Thr His Lys Asp Ala Glu Ile Leu Ser His Val
                85                  90                  95

Phe Gln Trp Leu Gly Phe Thr Val His Ile His Asn Asn Val Thr Lys
            100                 105                 110

Val Glu Met Glu Met Val Leu Gln Lys Gln Lys Cys Asn Pro Ala His
        115                 120                 125

Ala Asp Gly Asp Cys Phe Val Phe Cys Ile Leu Thr His Gly Arg Phe
    130                 135                 140

Gly Ala Val Tyr Ser Ser Asp Glu Ala Leu Ile Pro Ile Arg Glu Ile
145                 150                 155                 160

Met Ser His Phe Thr Ala Leu Gln Cys Pro Arg Leu Ala Glu Lys Pro
                165                 170                 175

Lys Leu Phe Phe Ile Gln Ala Cys Gln Gly Glu Ile Gln Pro Ser
            180                 185                 190

Val Ser Ile Glu Ala Glu Asn Leu Tyr Phe Gln
        195                 200

<210> SEQ ID NO 16
<211> LENGTH: 102
<212> TYPE: PRT
<213> ORGANISM: Artificial sequence
<220> FEATURE:
<223> OTHER INFORMATION: Cleaved part of caspase 10 by TEV

<400> SEQUENCE: 16

Gly Gln Ala Pro Thr Ser Leu Gln Asp Ser Ile Pro Ala Glu Ala Asp
1               5                   10                  15

Phe Leu Leu Gly Leu Ala Thr Val Pro Gly Tyr Val Ser Phe Arg His
            20                  25                  30

Val Glu Glu Gly Ser Trp Tyr Ile Gln Ser Leu Cys Asn His Leu Lys
        35                  40                  45

Lys Leu Val Pro Arg Met Leu Lys Phe Leu Glu Lys Thr Met Glu Ile
    50                  55                  60

Arg Gly Arg Lys Arg Thr Val Trp Gly Ala Lys Gln Ile Ser Ala Thr
65                  70                  75                  80

Ser Leu Pro Thr Ala Ile Ser Ala Gln Thr Pro Arg Pro Met Arg
                85                  90                  95

Arg Trp Ser Ser Val Ser
            100

<210> SEQ ID NO 17
<211> LENGTH: 163
<212> TYPE: PRT
<213> ORGANISM: Homo sapiens

<400> SEQUENCE: 17

Met Ala Val Pro Ile Ala Gln Lys Ser Glu Pro His Ser Leu Ser Ser
1               5                   10                  15

Glu Ala Leu Met Arg Arg Ala Val Ser Leu Val Thr Asp Ser Thr Ser
            20                  25                  30

Thr Phe Leu Ser Gln Thr Thr Tyr Ala Leu Ile Glu Ala Ile Thr Glu
        35                  40                  45

Tyr Thr Lys Ala Val Tyr Thr Leu Thr Ser Leu Tyr Arg Gln Tyr Thr
50                  55                  60

Ser Leu Leu Gly Lys Met Asn Ser Glu Glu Asp Glu Val Trp Gln
65                  70                  75                  80

Val Ile Ile Gly Ala Arg Ala Glu Met Thr Ser Lys His Gln Glu Tyr
                85                  90                  95

Leu Lys Leu Glu Thr Thr Trp Met Thr Ala Val Gly Leu Ser Glu Met
            100                 105                 110

Ala Ala Glu Ala Ala Tyr Gln Thr Gly Ala Asp Gln Ala Ser Ile Thr
        115                 120                 125

Ala Arg Asn His Ile Gln Leu Val Lys Leu Gln Val Glu Glu Val His
    130                 135                 140

Gln Leu Ser Arg Lys Ala Glu Thr Lys Leu Ala Glu Ala Gln Ile Glu
145                 150                 155                 160

Glu Leu Arg

<210> SEQ ID NO 18
<211> LENGTH: 301
<212> TYPE: PRT
<213> ORGANISM: Homo sapiens

<400> SEQUENCE: 18

Met Glu Gly Asp Phe Ser Val Cys Arg Asn Cys Lys Arg His Val Val
1               5                   10                  15

Ser Ala Asn Phe Thr Leu His Glu Ala Tyr Cys Leu Arg Phe Leu Val
            20                  25                  30

Leu Cys Pro Glu Cys Glu Glu Pro Val Pro Lys Glu Thr Met Glu Glu
        35                  40                  45

His Cys Lys Leu Glu His Gln Gln Val Gly Cys Thr Met Cys Gln Gln
    50                  55                  60

Ser Met Gln Lys Ser Ser Leu Glu Phe His Lys Ala Asn Glu Cys Gln
65                  70                  75                  80

Glu Arg Pro Val Glu Cys Lys Phe Cys Lys Leu Asp Met Gln Leu Ser
                85                  90                  95

Lys Leu Glu Leu His Glu Ser Tyr Cys Gly Ser Arg Thr Glu Leu Cys
            100                 105                 110

Gln Gly Cys Gly Gln Phe Ile Met His Arg Met Leu Ala Gln His Arg
        115                 120                 125

Asp Val Cys Arg Ser Glu Gln Ala Gln Leu Gly Lys Gly Glu Arg Ile
    130                 135                 140

Ser Ala Pro Glu Arg Glu Ile Tyr Cys His Tyr Cys Asn Gln Met Ile
145                 150                 155                 160

Pro Glu Asn Lys Tyr Phe His His Met Gly Lys Cys Cys Pro Asp Ser

```
                    165                 170                 175
Glu Phe Lys Lys His Phe Pro Val Gly Asn Pro Glu Ile Leu Pro Ser
            180                 185                 190
Ser Leu Pro Ser Gln Ala Ala Glu Asn Gln Thr Ser Thr Met Glu Lys
        195                 200                 205
Asp Val Arg Pro Lys Thr Arg Ser Ile Asn Arg Phe Pro Leu His Ser
    210                 215                 220
Glu Ser Ser Lys Lys Ala Pro Arg Ser Lys Asn Lys Thr Leu Asp
225                 230                 235                 240
Pro Leu Leu Met Ser Glu Pro Lys Pro Arg Thr Ser Ser Pro Arg Gly
            245                 250                 255
Asp Lys Ala Ala Tyr Asp Ile Leu Arg Arg Cys Ser Gln Cys Gly Ile
        260                 265                 270
Leu Leu Pro Leu Pro Ile Leu Asn Gln His Gln Glu Lys Cys Arg Trp
    275                 280                 285
Leu Ala Ser Ser Lys Gly Lys Gln Val Arg Asn Phe Ser
290                 295                 300
```

<210> SEQ ID NO 19
<211> LENGTH: 1147
<212> TYPE: PRT
<213> ORGANISM: Artificial
<220> FEATURE:
<223> OTHER INFORMATION: fusion proetin

<400> SEQUENCE: 19

```
Met Glu Asn Thr Glu Asn Ser Val Asp Ser Lys Ser Ile Lys Asn Leu
1               5                   10                  15
Glu Pro Lys Ile Ile His Gly Ser Glu Ser Met Asp Ser Gly Ile Ser
            20                  25                  30
Leu Asp Asn Ser Tyr Lys Met Asp Tyr Pro Glu Met Gly Leu Cys Ile
        35                  40                  45
Ile Ile Asn Asn Lys Asn Phe His Lys Ser Thr Gly Met Thr Ser Arg
    50                  55                  60
Ser Gly Thr Asp Val Asp Ala Ala Asn Leu Arg Glu Thr Phe Arg Asn
65                  70                  75                  80
Leu Lys Tyr Glu Val Arg Asn Lys Asn Asp Leu Thr Arg Glu Glu Ile
                85                  90                  95
Val Glu Leu Met Arg Asp Val Ser Lys Glu Asp His Ser Lys Arg Ser
            100                 105                 110
Ser Phe Val Cys Val Leu Leu Ser His Gly Glu Glu Gly Ile Ile Phe
        115                 120                 125
Gly Thr Asn Gly Pro Val Asp Leu Lys Lys Ile Thr Asn Phe Phe Arg
    130                 135                 140
Gly Asp Arg Cys Arg Ser Leu Thr Gly Lys Pro Lys Leu Phe Ile Ile
145                 150                 155                 160
Gln Ala Cys Arg Cys Thr Glu Leu Asp Cys Gly Ile Glu Thr Glu Asn
                165                 170                 175
Leu Tyr Phe Gln Ser Gly Val Asp Asp Met Ala Cys His Lys Ile
            180                 185                 190
Pro Val Glu Ala Asp Phe Leu Tyr Ala Tyr Ser Thr Ala Pro Gly Tyr
        195                 200                 205
Tyr Ser Trp Arg Asn Ser Lys Asp Gly Ser Trp Phe Ile Gln Ser Leu
    210                 215                 220
Cys Ala Met Leu Lys Gln Tyr Ala Asp Lys Leu Glu Phe Met His Ile
```

```
            225                 230                 235                 240
        Leu Thr Arg Val Asn Arg Lys Val Ala Thr Glu Phe Glu Ser Phe Ser
                        245                 250                 255
        Phe Asp Ala Thr Phe His Ala Lys Lys Gln Ile Pro Cys Ile Val Ser
                        260                 265                 270
        Met Leu Thr Lys Glu Leu Tyr Phe Tyr His Gly Ala Gly Ala Gly Asp
                        275                 280                 285
        Tyr Lys Asp Asp Asp Lys Gly Asp Tyr Lys Asp Asp Asp Lys
                        290                 295                 300
        Ala Ala Ala Gly Gly Glu Asn Leu Tyr Phe Gln Ala Gly Ala Gly Ala
        305                 310                 315                 320
        Met Gly Ala Gly Ala Gly Glu Asn Leu Tyr Phe Gln Ala Asp Asp Gln
                        325                 330                 335
        Gly Cys Ile Glu Glu Gln Gly Val Glu Asp Ser Ala Asn Glu Asp Ser
                        340                 345                 350
        Val Asp Ala Lys Pro Asp Arg Ser Ser Phe Val Pro Ser Leu Phe Ser
                        355                 360                 365
        Lys Lys Lys Lys Asn Val Thr Met Arg Ser Ile Lys Thr Thr Arg Asp
                        370                 375                 380
        Arg Val Pro Thr Tyr Gln Tyr Asn Met Asn Phe Glu Lys Leu Gly Lys
        385                 390                 395                 400
        Cys Ile Ile Ile Asn Asn Lys Asn Phe Asp Lys Val Thr Gly Met Gly
                        405                 410                 415
        Val Arg Asn Gly Thr Asp Lys Asp Ala Glu Ala Leu Phe Lys Cys Phe
                        420                 425                 430
        Arg Ser Leu Gly Phe Asp Val Ile Val Tyr Asn Asp Cys Ser Cys Ala
                        435                 440                 445
        Lys Met Gln Asp Leu Leu Lys Lys Ala Ser Glu Glu Asp His Thr Asn
                        450                 455                 460
        Ala Ala Cys Phe Ala Cys Ile Leu Leu Ser His Gly Glu Glu Asn Val
        465                 470                 475                 480
        Ile Tyr Gly Lys Asp Gly Val Thr Pro Ile Lys Asp Leu Thr Ala His
                        485                 490                 495
        Phe Arg Gly Asp Arg Cys Lys Thr Leu Leu Glu Lys Pro Lys Leu Phe
                        500                 505                 510
        Phe Ile Gln Ala Cys Arg Gly Thr Glu Leu Asp Asp Gly Ile Gln Ala
                        515                 520                 525
        Glu Asn Leu Tyr Phe Gln Ser Gly Pro Ile Asn Asp Thr Asp Ala Asn
                        530                 535                 540
        Pro Arg Tyr Lys Ile Pro Val Glu Ala Asp Phe Leu Phe Ala Tyr Ser
        545                 550                 555                 560
        Thr Val Pro Gly Tyr Tyr Ser Trp Arg Ser Pro Gly Arg Gly Ser Trp
                        565                 570                 575
        Phe Val Gln Ala Leu Cys Ser Ile Leu Glu Glu His Gly Lys Asp Leu
                        580                 585                 590
        Glu Ile Met Gln Ile Leu Thr Arg Val Asn Asp Arg Val Ala Arg His
                        595                 600                 605
        Phe Glu Ser Gln Ser Asp Asp Pro His Phe His Glu Lys Lys Gln Ile
                        610                 615                 620
        Pro Cys Val Val Ser Met Leu Thr Lys Glu Leu Tyr Gly Phe Ser Gln
        625                 630                 635                 640
        Gly Gly Gly Ala Ala Ala Gly Ala Gly Ala Gly Asp Tyr Lys Asp Asp
                        645                 650                 655
```

```
Asp Asp Lys Gly Asp Tyr Lys Asp Asp Asp Lys Ala Ala Ala Gly
            660                 665                 670

Gly Glu Asn Leu Tyr Phe Gln Ala Gly Ala Gly Ala Met Ala Val Pro
                675                 680                 685

Ile Ala Gln Lys Ser Glu Pro His Ser Leu Ser Glu Ala Leu Met
            690                 695                 700

Arg Arg Ala Val Ser Leu Val Thr Asp Ser Thr Ser Thr Phe Leu Ser
705                 710                 715                 720

Gln Thr Thr Tyr Ala Leu Ile Glu Ala Ile Thr Glu Tyr Thr Lys Ala
                725                 730                 735

Val Tyr Thr Leu Thr Ser Leu Tyr Arg Gln Tyr Thr Ser Leu Leu Gly
                740                 745                 750

Lys Met Asn Ser Glu Glu Glu Asp Glu Val Trp Gln Val Ile Ile Gly
            755                 760                 765

Ala Arg Ala Glu Met Thr Ser Lys His Gln Glu Tyr Leu Lys Leu Glu
            770                 775                 780

Thr Thr Trp Met Thr Ala Val Gly Leu Ser Glu Met Ala Ala Glu Ala
785                 790                 795                 800

Ala Tyr Gln Thr Gly Ala Asp Gln Ala Ser Ile Thr Ala Arg Asn His
                805                 810                 815

Ile Gln Leu Val Lys Leu Gln Val Glu Glu Val His Gln Leu Ser Arg
            820                 825                 830

Lys Ala Glu Thr Lys Leu Ala Glu Ala Gln Ile Glu Glu Leu Arg Gly
            835                 840                 845

Ala Gly Ala Gly Asp Tyr Lys Asp Asp Asp Lys Gly Asp Tyr Lys
            850                 855                 860

Asp Asp Asp Lys Ala Ala Ala Gly Gly Glu Asn Leu Tyr Phe Gln
865                 870                 875                 880

Ala Gly Ala Gly Ala Met Glu Asn Leu Tyr Phe Gln Ser Ala Gly Ala
                885                 890                 895

Gly Ala Gly Glu Ser Leu Phe Lys Gly Pro Arg Asp Tyr Asn Pro Ile
            900                 905                 910

Ser Ser Thr Ile Cys His Leu Thr Asn Glu Ser Asp Gly His Thr Thr
            915                 920                 925

Ser Leu Tyr Gly Ile Gly Phe Gly Pro Phe Ile Ile Thr Asn Lys His
            930                 935                 940

Leu Phe Arg Arg Asn Asn Gly Thr Leu Leu Val Gln Ser Leu His Gly
945                 950                 955                 960

Val Phe Lys Val Lys Asp Thr Thr Thr Leu Gln Gln His Leu Ile Asp
                965                 970                 975

Gly Arg Asp Met Met Ile Ile Arg Met Pro Lys Asp Phe Pro Pro Phe
            980                 985                 990

Pro Gln Lys Leu Lys Phe Arg Glu Pro Gln Arg Glu Glu Arg Ile Cys
            995                 1000                1005

Leu Val Thr Thr Asn Phe Gln Ala Lys Ser Met Ser Ser Met Val
            1010                1015                1020

Ser Asp Thr Ser Cys Thr Phe Pro Ser Ser Asp Gly Ile Phe Trp
            1025                1030                1035

Lys His Trp Ile Gln Thr Lys Asp Gly Gln Cys Gly Ser Pro Leu
            1040                1045                1050

Val Ser Thr Arg Asp Gly Phe Ile Val Gly Ile His Ser Ala Ser
            1055                1060                1065
```

-continued

```
Asn Phe Thr Asn Thr Asn Asn Tyr Phe Thr Ser Val Pro Lys Asn
    1070            1075            1080

Phe Met Glu Leu Leu Thr Asn Gln Glu Ala Gln Gln Trp Val Ser
    1085            1090            1095

Gly Trp Arg Leu Asn Ala Asp Ser Val Leu Trp Gly Gly His Lys
    1100            1105            1110

Val Phe Met Val Lys Pro Glu Glu Pro Phe Gln Pro Val Lys Glu
    1115            1120            1125

Ala Thr Gln Leu Met Asn Glu Leu Val Tyr Ser Gln Gly Ala Gly
    1130            1135            1140

Ala Gly Ala Gly
    1145
```